US008398592B2

(12) United States Patent
Leibner-Druska (10) Patent No.: US 8,398,592 B2
(45) Date of Patent: Mar. 19, 2013

(54) MEDICATION DATA TRANSFER SYSTEM AND METHOD FOR PATIENT INFUSIONS

(76) Inventor: Thomas Leibner-Druska, Grevenbroich (DE)

( * ) Notice: Subject to any disclaimer, the term of this patent is extended or adjusted under 35 U.S.C. 154(b) by 2821 days.

(21) Appl. No.: 10/935,369

(22) Filed: Sep. 7, 2004

(65) Prior Publication Data

US 2006/0100746 A1    May 11, 2006

(51) Int. Cl.
*A61M 37/00* (2006.01)
(52) U.S. Cl. ........... 604/131; 705/2; 604/65; 604/66; 604/67; 604/151; 604/189; 604/500; 283/70; 702/177; 600/522; 417/18
(58) Field of Classification Search ............ 604/131, 604/65–67, 151, 189, 500; 705/2; 283/70; 600/522; 702/177; 417/18
See application file for complete search history.

(56) References Cited

U.S. PATENT DOCUMENTS

| | | | | |
|---|---|---|---|---|
| 4,925,444 A * | 5/1990 | Orkin et al. | ............ | 604/80 |
| 5,104,374 A * | 4/1992 | Bishko et al. | ............ | 604/31 |
| 5,207,642 A * | 5/1993 | Orkin et al. | ............ | 604/65 |
| 5,319,363 A * | 6/1994 | Welch et al. | ............ | 340/825.36 |
| 5,378,231 A * | 1/1995 | Johnson et al. | ............ | 604/67 |
| 5,643,212 A * | 7/1997 | Coutre et al. | ............ | 604/131 |
| 5,681,285 A * | 10/1997 | Ford et al. | ............ | 604/151 |
| 5,713,856 A * | 2/1998 | Eggers et al. | ............ | 604/65 |
| 5,772,635 A * | 6/1998 | Dastur et al. | ............ | 604/131 |
| 5,781,442 A * | 7/1998 | Engleson et al. | ............ | 700/214 |
| 6,070,761 A * | 6/2000 | Bloom et al. | ............ | 222/81 |
| 6,519,569 B1 * | 2/2003 | White et al. | ............ | 705/3 |
| 6,671,563 B1 | 12/2003 | Engelson et al. | | |
| 6,731,989 B2 | 5/2004 | Engleson et al. | | |
| 6,790,198 B1 * | 9/2004 | White et al. | ............ | 604/151 |
| 2002/0038392 A1 | 3/2002 | De La Huerga | | |
| 2002/0169636 A1 * | 11/2002 | Eggers et al. | ............ | 705/3 |
| 2004/0073329 A1 | 4/2004 | Engleson et al. | | |
| 2004/0128162 A1 | 7/2004 | Schlotterbeck et al. | | |
| 2004/0143459 A1 | 7/2004 | Engleson et al. | | |

FOREIGN PATENT DOCUMENTS

| | | |
|---|---|---|
| JP | 2002-336352 | 11/2002 |
| JP | 2002-336353 | 11/2002 |

(Continued)

OTHER PUBLICATIONS

Office Action dated Nov. 16, 2010 from related Japanese Application No. 2007-530491.

*Primary Examiner* — Nicholas Lucchesi
*Assistant Examiner* — Scott Medway
(74) *Attorney, Agent, or Firm* — McDermott Will & Emery LLP (57) ABSTRACT

A system and method are provided to associate a medication name with an infusion pump and to communicate that association to a patient data management system ("PDMS") for display and monitoring. In the case where the infusion pump does not contain a library of selectable medical fluid names that includes the name of the medical fluid to be infused, a separate computer will display a list of medical fluid names for the infusion pump and the operator may select the name of the medical fluid for that infusion pump. The computer will then continually associate that medical fluid name with that infusion pump and communicate the association to the PDMS. In the case where the infusion pump is capable of accepting an upload of new medical fluid names, the computer will upload an abbreviated list of fluid names so as not to overburden the computer with the transfer of large amounts of data.

26 Claims, 5 Drawing Sheets

FOREIGN PATENT DOCUMENTS

| WO | WO 96/28209 | 9/1996 |
| WO | WO 96/36389 | 11/1996 |
| WO | WO 02/36044 A2 | 5/2002 |
| WO | WO 02/69099 A2 | 9/2002 |
| WO | WO 03/092769 A2 | 11/2003 |
| WO | WO 2004/070994 | 8/2004 |

* cited by examiner

MEDICATION DATA TRANSFER SYSTEM AND METHOD FOR PATIENT INFUSIONS

BACKGROUND OF THE INVENTION

The present invention generally relates to controlling the transfer of medication data, and more particularly, to a system and a method for transferring medication data between medical infusion pumps and patient data management systems.

Patient data management systems ("PDMS") have provided a significant advance in the field of patient care. Such systems typically comprise a network of interconnected computers located in a health care facility that store and make available numerous data concerning the patients and medications of the facility. Data ranging from administrative data to vital signs data, to the status of ongoing medical fluid infusions are typically available at one or more computers or displays of the PDMS network. In one well-known system, a central server or servers are connected to a physician order entry ("POE") system computer, computers, or other device. The central server or servers are also connected to the pharmacy information system ("PIS") computer, computers, or other device, and also to a series of bedside computers. In a more complete version of such a PDMS, each bedside has its own computer forming a part of the PDMS.

Patient data management systems, such as the one discussed briefly above, have become highly desirable in the busy health care facilities typical today. Under today's conditions, nurses have much to do and systems such as these are meant to make the nurse's job easier by automatically correlating patient information and updating patient records as well as providing means to avoid medication errors. Today, the PDMS attempts to provide a single location at which all patient-related data can be viewed by the nurse as desired. Additionally, the interfaces between the nurses and the PDMS have been improved. More and more PDMS attempt to provide nurses with choices to select when inputting data as opposed to requiring manual text data input. While the ability to select data is not error proof, but it provides a much improved process over manual text input. An example is the selection of a medical fluid name to be infused into a patient. Selecting the medical fluid name from a list generally allows for faster and more accurate input of data while avoiding spelling errors should the medical fluid name be typed manually by the nurse.

Many PDMS make available general information about the patients as well as specific infusion information. Such information includes physical data about a patient such as weight, age, and allergies. Data also may include vital signs, such as temperature, blood pressure, and other. Also available can be the list of prescriptions and medications for the patient, whether they are past, present, or future. In the PDMS discussed above, the bedside computer may comprise a sophisticated monitor, such as a liquid crystal color display with graphics capability such that large amounts of data may be presented as selected by the nurse or physician, but at the same time may comprise a relatively older technology processor that is incapable of a large instantaneous flows of data. Requesting large amounts of data to be transferred through such older technology processors can cause the processor to function poorly or even "crash."

Another part of the patient medication system in a health care facility is the infusion pump. In many cases, physicians prescribe the administration of medical fluids, such as a drug, to a patient through the use of an infusion pump. Infusion pumps are capable of very accurate administration of medical fluids to a patient over long periods of time. Their use is preferred in many cases where the accurate administration of a drug is necessary to obtain the optimum treatment effects of the drug. However infusion pumps must be programmed with the infusion parameters, the programming checked, and the infusion monitored during the course of the infusion. Patients may have six or more such infusions occurring simultaneously. Such activities typically comprise a part of the duties of a nurse. They require the nurse to monitor both the display of the PDMS for certain patient data and to monitor the display of the infusion pump or pumps.

One goal of many health care facilities is to provide increased "connectivity" between all medical devices with the PDMS. Such increased connectivity would permit the nurse to monitor only one display; i.e., the PDMS display, to view patient information thereby lessening the time nurses must take to monitor patient-specific data. Health care facilities have been requesting that infusion pumps, as well as other medical instruments, increase their connectivity capabilities so that they can share data with the PDMS. In any case, health care facilities desire that the PDMS be able to present infusions underway at the PDMS display so that at one glance, nurses can check on the status of a patient's treatment.

While almost every infusion pump includes a front panel data display, which displays data in text, graphics, or both, not all infusion pumps offer comprehensive lists of drug names for this display. In those that do, the nurse may select the name of the drug being infused to the patient from the list of drug names in the infusion pump. That drug name will then appear on the infusion pump display as the infusion progresses. Even if the pump display does not include the name of the drug currently being infused, many health care facilities require that the PDMS accurately display the name of the drug. Optimally, when the pump is being programmed, the nurse or operator selects the correct name of the drug from the pump display and the pump, through connectivity with the PDMS, then informs the PDMS of the correct drug name. The PDMS then displays the same, and correct, drug name associated with this pump. However, even if the pump does not have the means to display certain drug names, the health care facility may require that at least the PDMS must. To require the nurse that programmed the pump to then access the PDMS and type the name of the drug into the PDMS and associate it with this particular infusion pump adds duties to the nurse's already busy schedule. Further, there is a potential source of errors in infusion medication and its documentation, because the nurse can mismatch the particular pump and its assigned drug name. It would be desirable to have such a process made easier for nurses and safer for patients.

The list of drugs available for use in treating patients in health care facilities today is extensive, numbering in the thousands. Even so, some physicians prescribe some custom medical drugs not on such common lists. These custom medical drugs may be combinations of known drugs with a name reflecting the names of the drugs combined. Although these custom drugs are not on the extensive drug list, they are easy enough to prepare by the pharmacy and the PDMS is able to easily accommodate and display such drug names. However, infusion pumps, with their limited memories and limited connectivity for data transfer, are often unable to store such custom drug names or even extensive lists of thousands of drugs at this time. Yet the ability to display on the pump screen the drug being infused or at least to indicate on the display of the PDMS precisely which drug each infusion pump is infusing to the patient is desired, or even required, by health care facilities today.

Because the list of medical drugs commonly available today is so large, it can take additional time just for the mechanical process of scrolling through a drug list to find the name of a pertinent drug. Even though the process has been made faster by means such as alphabetizing the drug names and classifying them into categories or "pages" so that one may quickly go to more focused sub-lists to select the pertinent drug, the process still requires significant amounts of time. Thus some health care facilities have compiled a "standard" list of the one-hundred common medical drugs used in that facility. This substantially reduces the amount of time necessary to find a particular drug likely to be used in that facility and results in a much lower amount of data should the list need to be transferred among the various devices forming a part of the PDMS, including infusion pumps. However, such list often does not include custom drugs prescribed by physicians.

For those pumps that do not have the extensive list of drugs, they will work fine after being programmed and can infuse the drug installed in the pump even though the name of the drug is not displayed on the pump. In such a case, the only way to find out what drug is being infused is to look at the label on the bag of medical drug. This requires information gathering which also adds time to the nurse's duties and is not desirable Some pumps include a bar code system that is used to assist in providing data to the pump concerning the drug name being infused and in some cases, the actual pumping parameters for that pump and patient. While such a system could assist in data transfer under certain conditions, some health care facilities do not agree with using bar codes. Bar codes have been found to become inaccurate or unusable due to smudging, misplacement, obliteration, or other alterations that can easily occur in an intense medical care environment. It is also undesirable to have the necessity of printing bar code labels before using them since such efforts add to an already busy workload for nurses.

Therefore, a need exists in the art for a system and method by which the drugs being infused to a patient by infusion pumps be indicated to the PDMS so that such drugs can be displayed at the PDMS for reducing the time nurses need to spend in monitoring patients. The present invention fulfills these needs and others.

SUMMARY OF THE INVENTION

Briefly and in general terms, the present invention is directed to a system and method for providing medical fluid data relevant to the operation of a medical device connected to a patient. The system and method of the present invention obtain patient-specific data from another source or sources relevant to the medical device used to infuse a medical fluid into the patient, display that data for selection by an operator, and upon selection by the operator, associate that data with the specific medical device.

In a more detailed aspect, the system and method in accordance with the invention detects the connection of an infusion pump to a patient, obtains patient prescriptions from another data source, displays those prescriptions for selection by a care giver, and associates the selected prescription with the pump.

In a further aspect, the system and method of the invention detect that a pump has been started for infusion of a drug into a patient, but that the pump has not provided a drug name for the medical fluid being infused into the patient. The health care facility's standard list of drug names is obtained from a patient data management system ("PDMS") and in another aspect, the names of drugs prescribed for the patient are obtained from the PDMS. These lists are displayed in a window on the PDMS bedside computer. In a more detailed aspect, the system and method in accordance with the invention also displays all pumps that are located for the patient's use and encircles in a blinking yellow line the ones that are presently operating without a drug name. In another embodiment, the PDMS may flash an icon for a pump and provide an alert for that pump such as "NO DRUG NAME" to alert the nurse that the medical fluid infused by the pump has not been identified to the PDMS. The data transfer system and method then allows the nurse to match the flashing pump with a drug name (medical fluid name) on the pop up window of listed drug names. The nurse selects the drug name, and then the data transfer program associates it with that pump in a data base associated with the data transfer system and communicates that drug name and associated pump and patient to the PDMS for display.

In a further aspect, the name of the medical fluid for infusion into the patient may be uploaded to the pump as well as a pumping parameter or parameters. The uploaded parameter or parameters are used to program the pump for operation. In another aspect, an entire infusion protocol is uploaded to the pump and programs the pump for operation.

A method of associating a name for a medical fluid with an identification of an infusion pump used to infuse the medical fluid into a patient comprises identifying an infusion pump as being connected to the patient, monitoring the infusion pump for an indication by the infusion pump of the name of the medical fluid for infusion into the patient, displaying at least one selectable medical fluid name on a monitor that is separately located from the infusion pump, selecting a medical fluid name displayed on the separate monitor, associating the selected medical fluid name with the identification of the infusion pump, and providing the selected medical fluid name and the identification of the infusion pump to a patient data management system ("PDMS") for display of the selected medical fluid name and associated identification of the infusion pump on a monitor that is separately located from the infusion pump. In other aspects, the step of monitoring the infusion pump also comprises monitoring the infusion pump with a computer external from the infusion pump for an indication of a start of an infusion into the patient, and upon detecting the indication of start of infusion, then performing the step of associating the selected medical fluid name with the identification of the infusion pump.

In further more detailed aspects, the indication of the start of an infusion is detected when a start infusion switch is pressed on the infusion pump. The step of displaying at least one selectable medical fluid name on a separate monitor comprises displaying a list of medical fluid names that have been prescribed for the patient. The step of displaying at least one selectable medical fluid name on a separate monitor comprises displaying a list of names of standard medical fluids. The step of displaying a list of standard medical fluid names comprises displaying an abbreviated list of medical fluid names selected by a health care facility in which the infusion pump is located. The method further comprises associating at least one pumping parameter with the name of the medical fluid to be infused into the patient and wherein the step of providing the medical fluid name and identification of the infusion pump also further comprises providing the associated pumping parameter to the PDMS for display of the medical fluid name, associated identification of the infusion pump, and associated pumping parameter on the separate monitor.

In additional detailed aspects of the invention, after the step of selecting a medical fluid name displayed on the separate monitor, then uploading the selected medical fluid name to the pump, assigning at the pump the uploaded medical fluid name to the medical fluid being infused to the patient, communicating the uploaded medical fluid name by the pump to the PDMS, and associating the selected medical fluid name with the identification of the infusion pump at the PDMS for display of the uploaded medical fluid name and associated identification of the infusion pump on the separately-located monitor. In yet other aspects, the step of uploading the selected medical fluid name to the pump comprises abbreviating the selected medical fluid name to a smaller number of characters when the number of characters in the non-abbreviated medical fluid name exceeds a predetermined limit number, and adding a code to the abbreviated name that is unique to the non-abbreviated medical fluid name before uploading the medical fluid name to the pump. The method further comprises the step of comparing at the pump the abbreviated name and code uploaded to the pump to a table stored in the pump that contains such abbreviated names and codes corresponding to the non-abbreviated medical fluid names, in which table different medical fluid names may have identical abbreviated names but the codes are always different to thereby distinguish between different medical fluid names having the same abbreviated names.

In further aspects, the method further comprises uploading at least one pumping parameter to the pump, programming the pump with the uploaded pumping parameter for infusing the medical fluid to the patient, communicating the uploaded pumping parameter to the PDMS, and associating the selected pumping parameter with the identification of the infusion pump and the selected medical fluid name at the PDMS for display of the uploaded medical fluid name, the pumping parameter, and associated identification of the infusion pump on the separately-located monitor. The method further comprises comparing the uploaded pumping parameter to a data base of predetermined pumping parameter limits and providing an alert if the uploaded pumping parameter is outside the limits. The method further comprises storing the data base of predetermined pumping parameter limits within the pump.

Other additional detailed aspects of the invention further comprise monitoring the infusion pump to obtain status of the infusion into the patient and if the infusion pump is disconnected from communication with the PDMS before the infusion is complete and is then reconnected with the PDMS: maintaining the association between the infusion pump and the medical fluid name if the status of the pump shows that neither a pumping parameter nor the patient nor the medical fluid name were changed during the time of communication disconnection; and canceling the association between the infusion pump and the medical fluid name if the status of the pump shows that a pumping parameter or the patient or the medical fluid name was changed during the time of communication disconnection. The step of monitoring the infusion pump to obtain the status of the infusion pump during a time of disconnection from the PDMS comprises monitoring a log of the infusion pump.

In aspects of the system, a fluid infusion monitoring system in which a name for a medical fluid is associated with an identification of an infusion pump used to infuse the medical fluid into a patient comprises a monitor separately located from the infusion pump; and a computer in communication with the infusion pump and in communication with a patient data management system, wherein the computer is programmed to: identify an infusion pump as being connected to the patient; monitor the infusion pump for an indication by the infusion pump of the name of the medical fluid for infusion into the patient; display at least one selectable medical fluid name on the separately-located monitor; select a medical fluid name displayed on the separately-located monitor; associate the selected medical fluid name with the identification of the infusion pump; and provide the selected medical fluid name and the identification of the infusion pump to a patient data management system ("PDMS") for display of the selected medical fluid name and associated identification of the infusion pump on a monitor that is separately located from the infusion pump.

In more detailed aspects, the computer is also programmed to monitor the infusion pump for an indication of a start of an infusion into the patient and upon detecting the indication of start of infusion, then associate the selected medical fluid name with the identification of the infusion pump. The infusion pump has a start infusion switch and the computer is programmed to monitor the infusion pump for the press of a start-infusion switch on the infusion pump to indicate the beginning of an infusion. The computer is further programmed to display a list of medical fluid names that have been prescribed for the patient on the separately-located monitor. The computer is further programmed to display a list of names of standard medical fluids on the separately-located monitor. The computer is programmed to display an abbreviated list of medical fluid names selected by a health care facility in which the infusion pump is located on the separately-located monitor.

In additional system aspects, the computer is further programmed to associate at least one pumping parameter with the name of the medical fluid to be infused into the patient and provide the associated pumping parameter to the PDMS for display of the medical fluid name, associated identification of the infusion pump, and associated pumping parameter on the separate monitor. The computer is further programmed to upload the selected medical fluid name displayed on the separate monitor to the pump. The computer is further programmed to abbreviate the selected medical fluid name to a smaller number of characters when the number of characters in the non-abbreviated medical fluid name exceeds a predetermined limit number, and add a code to the abbreviated name that is unique to the non-abbreviated medical fluid name before uploading the medical fluid name to the pump.

In further aspects, the system further comprises a table stored in the pump that contains such abbreviated names and codes corresponding to the non-abbreviated medical fluid names, in which table different medical fluid names may have identical abbreviated names but the codes are always different to thereby distinguish between different medical fluid names having the same abbreviated names. The computer is further programmed to upload at least one pumping parameter to the pump relevant to the selected medical fluid for infusion into the patient by the pump and associate the uploaded pumping parameter with the identification of the infusion pump and the selected medical fluid name at the PDMS for display of the uploaded medical fluid name, the pumping parameter, and associated identification of the infusion pump on the separately-located monitor.

In yet further system aspects in accordance with the invention, the system further comprises a data base of predetermined pumping parameter limits and a processor programmed to compare the uploaded pumping parameter to the data base and provide an alert if the uploaded pumping parameter is outside the limits. The data base of predetermined pumping parameter limits is stored within the pump. The computer is further programmed to monitor the infusion pump to obtain status of the infusion into the patient and if the infusion pump is disconnected from communication with the PDMS before the infusion is complete and is then reconnected with the PDMS, maintain the association between the infusion pump and the medical fluid name if the status of the pump shows that neither a pumping parameter nor the patient nor the medical fluid name were changed during the time of communication disconnection, and cancel the association between the infusion pump and the medical fluid name if the status of the pump shows that a pumping parameter or the patient or the medical fluid name was changed during the time of communication disconnection. The computer is programmed to monitor a log of the infusion pump to determine the status of the infusion pump during the time that it was disconnected from the PDMS.

These and other features and advantages of the present invention will become apparent from the following detailed description of the preferred embodiments which, taken in conjunction with the accompanying drawings, illustrate by way of example the principles of the invention.

DETAILED DESCRIPTION OF THE PREFERRED EMBODIMENTS

Figure 1:
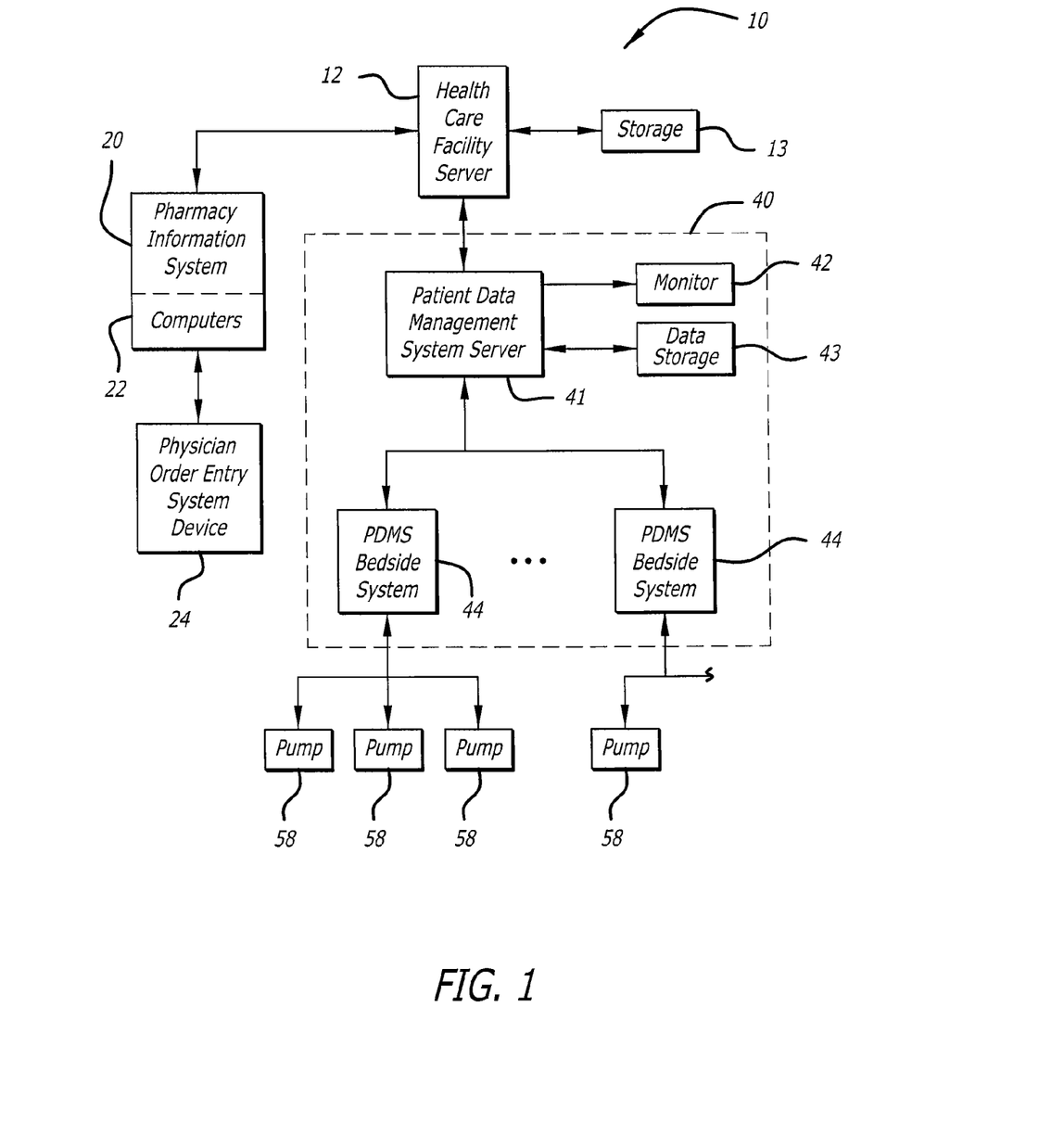
FIG. 1 is a block diagram representation of a care management system incorporating a patient data management system, a pharmacy information system, and physician order entry devices showing a PDMS bedside system located at infusion pumps.

Referring now in more detail to the drawings for purposes of illustration, wherein like reference numerals designate corresponding or like elements among the several views, there is generally shown in FIG. 1, an embodiment of a care management system 10 integrated into a hospital-wide information and care management system in accordance with aspects of the present invention. Referring now to FIG. 1, a block diagram of an embodiment of a care management system 10 is shown. In this embodiment, there is shown a health care facility server 12 with data storage 13 that may comprise a file server and memory used to store programs and data collected by various computers in a local or wide area network of the health care facility in which the care management system is located. The programs and data stored in the server 12 and storage 13 may include various administration data of the facility and the particular patients, and other data and programs. In the embodiment of FIG. 1, a pharmacy 20 is included at the health care facility and contains its own computer or computers 22. The prescriptions from physicians are forwarded to the pharmacy where the prescribed medical fluids are prepared for the patients and forwarded to the nurse stations 30 throughout the health care facility. Physicians may forward their prescriptions to the pharmacy through various means 24 such as a laptop computer, a personal digital assistant ("PDA"), or other means, wired or wireless. Such devices are well known to those skilled in the art thus no further description is provided here.

Figure 2:
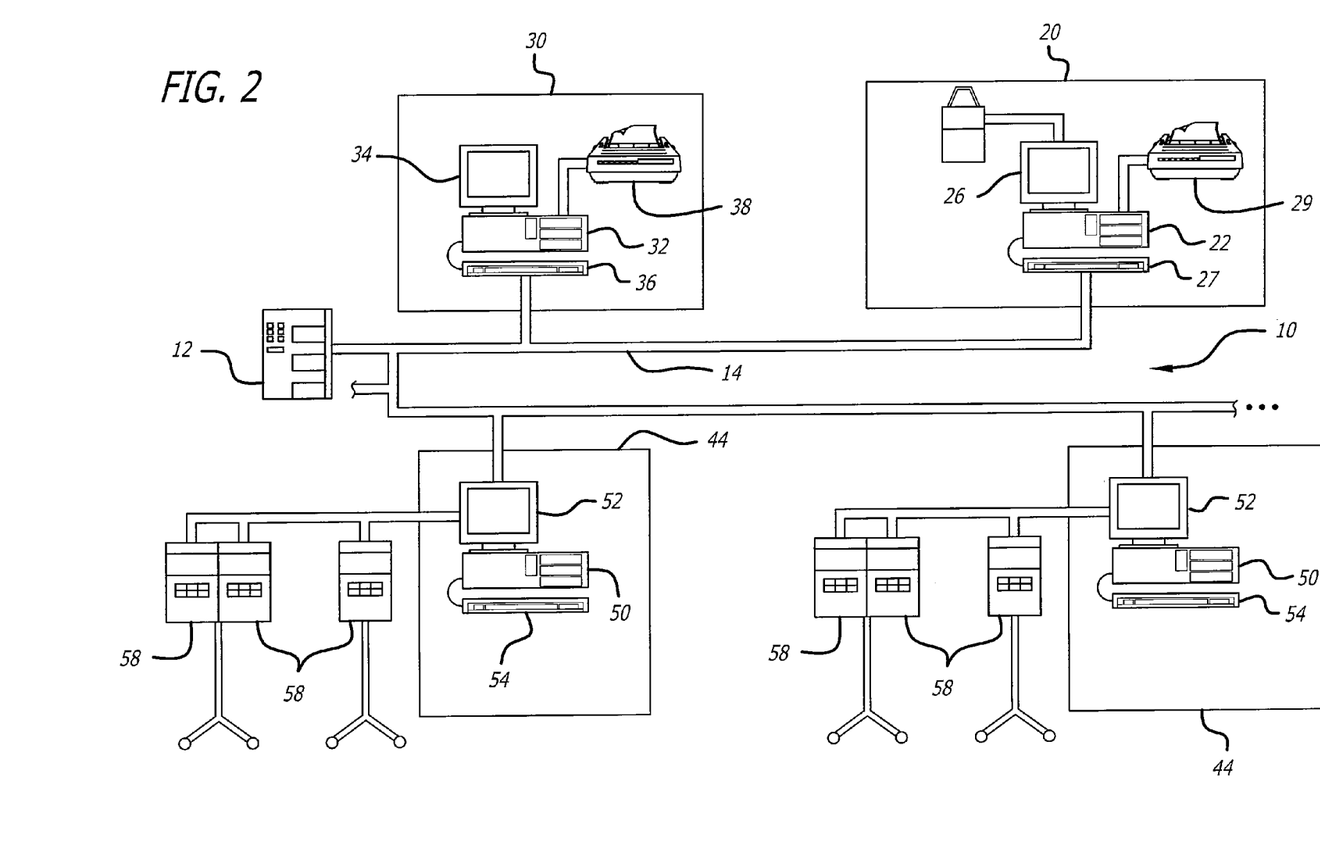
FIG. 2 is a block diagram of a care system similar to FIG. 1 additionally showing a network and hardware representations of devices, also showing the integration of the separate components.

Referring to FIGS. 1 and 2, the care management system 10 embodiment shown in FIG. 1 is depicted as being configured as a local area network with the file server 12 to which are connected the pharmacy system 20, the nursing station 30, and bedside CPUs 50. The file server 12 stores programs and data that have been input and collected by the various computers in the local area network 14. Various application modules of the care management system may be resident in each of the computers in the network and will be discussed in more detail below. Ethernet cabling of a local area network 14 is used to connect various CPUs to the file server in one embodiment. The file server 12 also has both local and network hard disk storage for storing programs as well as data gathered on the network.

Figure 3:
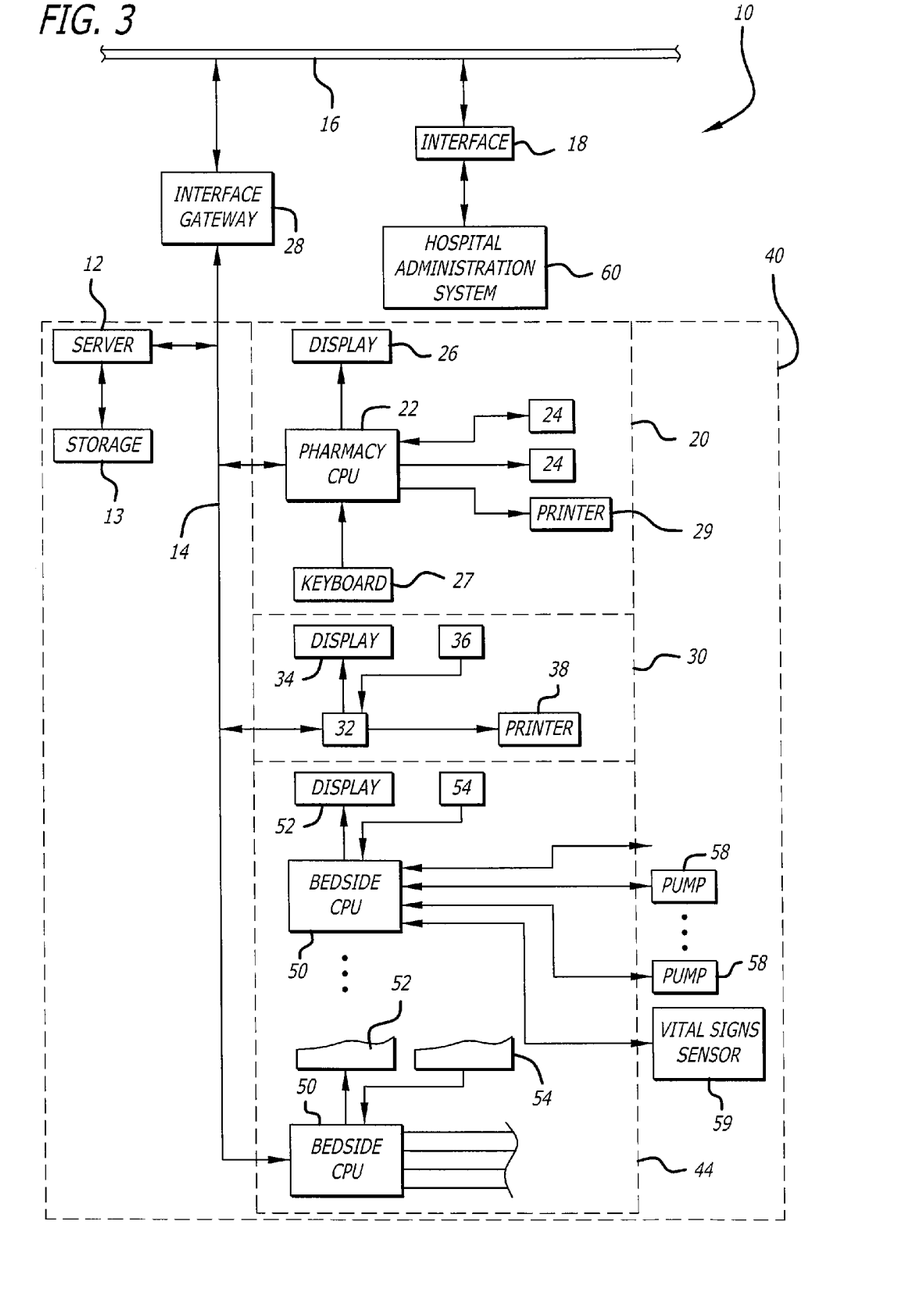
FIG. 3 is a further block diagram providing more detail than the diagram of FIG. 1 showing the integration of various devices and systems with networks.

A functional block diagram of the patient care management system 10 of FIGS. 1 and 2 is shown in FIG. 3 interfaced with and connected to other hospital information management systems to form an integrated information and care management system. This information and care management system is integrated with a combination of individual hospital systems, one of which is shown, i.e., the hospital administration system 60, and which are interconnected via a network 16 and appropriate interfaces 18. Other hospital systems may be interconnected, depending on the particular facility. Each of the various systems generally comprise a combination of hardware, such as digital computers, that may include one or more central processing units, high speed instruction and data storage, on-line mass storage of operating software and short term storage of data, off-line long-term storage of data, such as removable disk drive platters, CD ROMs, or magnetic tape, and a variety of communication ports for connecting to modems, local or wide area networks, such as the network 16, and printers for generating reports. Such systems may also include remote terminals that include video monitors and keyboards, touch screens, printers and interfaces to a variety of clinical devices. The operating systems and specific software applications will be described generally below.

The care management system 10 of FIGS. 2 and 3 includes a file server 12, such as an IBM or IBM-compatible personal computer having sufficient mass storage 13, such as local hard drives, CD ROM, magnetic tape, or other media, and appropriate communication interface capabilities to interconnect with other hardware comprising the care management system. Although many configurations are possible, in one embodiment the file server would include hardware such as a data communication router, a large hard drive to store data for the entire network, and communication hardware for communicating with the hospital network. Additionally, a separate computer (CPU) may be used to communicate with, control, and provide an interface gateway 28 to the hospital network 16.

The local area network 14 ("LAN"), comprising a thin net, or Ethernet cabling, or other communication means, wired or wireless, is used to connect the central file server 12 to the hardware that comprises the care management system 10. In the present embodiment, the file server 12 of the care management system is connected by the local area network (LAN) 14 to computers and other peripheral equipment located in the institution's pharmacy, at nursing stations located throughout the institution, and at the patient's bedside. In the embodiment shown, the module located in the pharmacy 20 comprises a central processing unit 22 to which is attached a video monitor 26 and a keyboard 27 for the entry and display of patient information and medical fluid or "drug" parameters. Also attached to the pharmacy CPU are various physician order or prescription entry devices 24. Also connected to the pharmacy CPU 22 is a general printer 29 used for generating reports containing information about patient history and/or patient treatment. The general printer 29 may be used to print labels, such as bar code labels, generated by the pharmacy CPU 22 after patient or drug data is input by a technician or pharmacist into the pharmacy computer 22 using the keyboard 27 or other means. Although shown and described as only single devices, i.e., a single computer 22, single keyboard 27, single monitor 26, in FIG. 3, this is for the purpose of preserving clarity in the drawing and description. More of each of these devices, as well as others, may be included in a pharmacy depending on the size of the health care facility. Furthermore, the pharmacy 20 may be connected to the hospital network 16 rather than the LAN 14, but may communicate with the LAN through the interface gateway 28.

Referring again to FIG. 1, a patient data management system ("PDMS") 40 is connected with the health care facility server 12 and includes a PDMS server 41, a monitor 42, data storage 43, and bedside PDMS 44. Referring to FIG. 3, the bedside PDMS typically include a computer 50 with an integral processor, data storage, and a PDMS monitor 52 for displaying patient information. In some systems, each bed in the facility includes a PDMS bedside system 44. In the PDMS system shown in FIGS. 1 and 3, the bedside PDMS system 44 is connected with the infusion pumps 58 used on the patient. While in some cases, only one infusion pump is connected with a patient, in other cases, more, such as six, infusion pumps are connected to a single patient. The PDMS is connected to all pumps in this embodiment.

Referring now to FIGS. 2 and 3, another computer, herein referred to as the nursing CPU 32, is located at a nursing station 30. Nursing stations are typically located in various sections and/or floors of a hospital or clinic and typically provide a central location for record storage and monitoring for a number of patient beds. The nursing CPU located at the nurse station typically includes a video monitor 34 for displaying patient or other information pertaining to the operation of the particular unit of the institution, and a keyboard 36, and may include other devices such as a mouse, touch screen, or other means for entering patient data or specific commands instructing the nursing CPU to generate reports relating to either the patient's medical history or the course and progress of treatment for an individual patient on the attached printer 38 or on the video monitor. Wired and wireless systems may be used by the nurse, including personal digital assistants ("PDA"). The nursing station CPU may also generate other reports such as, for example, a printout of drugs scheduled to be administered to patients, productivity measurements such as, for example, the amount of time a nurse spends with a patient or other reports useful for assisting in the efficient operation of the particular unit or the hospital. For example, a report listing the actual times of administration versus the scheduled times for administration may be prepared to assist in evaluation of staffing requirements.

Each care unit associated with the nursing station typically comprises one of more patient beds located in private rooms, shared rooms, or open or semi-open wards that contain multiple beds. In accordance with an embodiment of the present invention, each private room, semi-private room, or ward area has at least one bedside CPU 50 for monitoring and treating one or more patients. Each bedside CPU 50 has a video monitor 52 and a keyboard 54, mouse, touch screen, or other device. The bedside CPU 50 can be used by a nurse, physician, or technician to access a variety of institutional databases to display a variety of information about a particular patient. This information can include an on-line, real-time, graphical patient medication administration record (MAR) that is derived from the patient's medication profile maintained by the hospital's pharmacy information system 20. The bedside CPU 50 also allows remote access to a patient's records stored by the file server 12 to display medication history for the patient. This medication history includes a listing of all drug or other treatments including past, present and future deliveries to the patient. Additionally in this embodiment, access to administration records of the hospital's administration system 60 is available through the network 16.

Each bedside CPU 50 can be connected through an appropriate interface to various equipment. For example, the bedside CPU can be connected to an infusion pump 58 for delivering medication to the patient in a predetermined, controlled manner; or sensors 59 that can automatically monitor a patient's vital signs and send signals representative of these vital signs to the computer through an appropriate interface for storage and later retrieval by a selected software application to provide a graphic display of the patient's vital signs during the course of treatment. A plurality of bedside PDMS 44 are shown in the drawing; however, more or fewer may exist depending on the particular system and hospital requirements.

Figure 4:
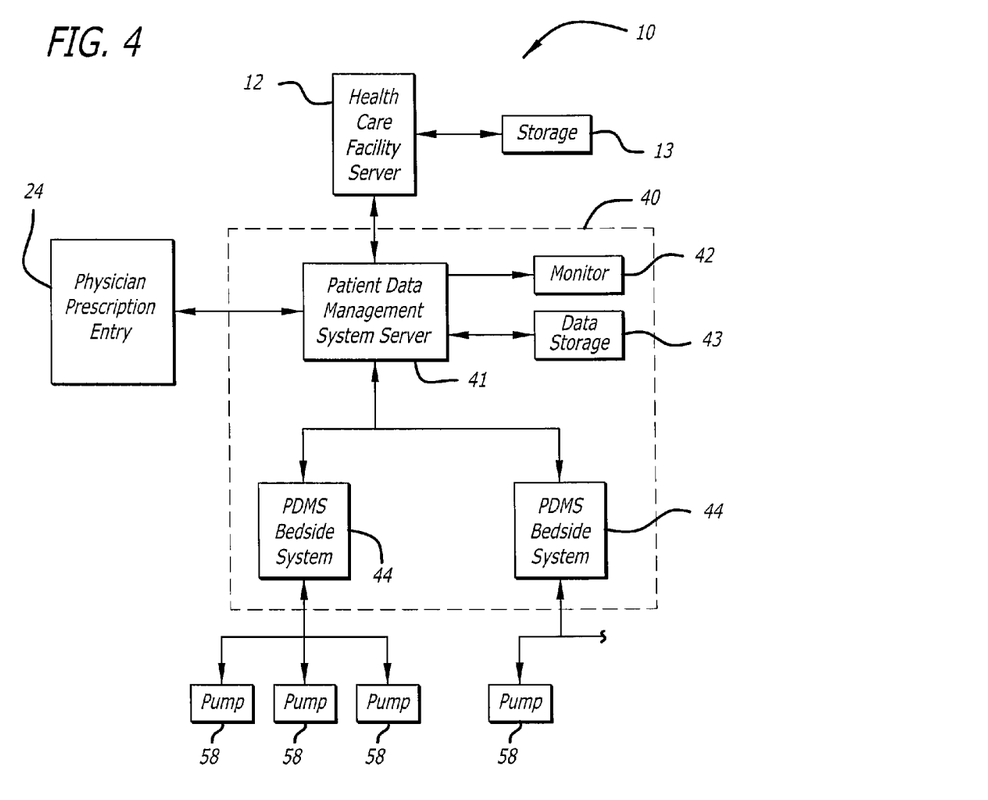
FIG. 4 presents a further block diagram of a patient data management system similar to FIG. 1 used in a health care facility that does not have a central pharmacy.

A similar care management system 10 is shown in FIG. 4 but does not include a pharmacy information system. This illustrated system is more likely to be found in European health care facilities where physicians forward their prescriptions through a physician prescription entry device 24 directly to a PDMS computer 41 in a patient data management system 40. Through the PDMS the main computer system 12 of the facility also receives the prescription for record-keeping purposes. Otherwise, the systems of FIGS. 1 and 4 are approximately the same.

Many of the above functions are now included in the PDMS. Such systems are well known to those skilled in the art and will not be described in great detail. As an example, please refer to the DIGISTAT™ PDMS from United Medical Software, srl at Loc. il Giuggiolo 1, 53036 Poggibonsi (SI), Italy, and the PDMS from Copra System GmbH, Allmendweg 8, 77887 Sasbachwalden, Germany, with a telephone no. of 49 78 41 27 00 22. These are examples only. Additionally, not all of the functions described above are available in many health care facilities. For example, in many European health care facilities, there is no central pharmacy.

Patient data management systems are similar to some of the configurations described above for nurses' stations. However PDMS typically have advanced programs permitting nurses and other health care professionals to access a wider array of data with selectable formats. Features are built into such systems to increase health care efficiency.

One purpose of the PDMS bedside system 44 of FIGS. 1 and 4 is to present as much data about a patient in the adjacent bed as is practical so that care givers need only refer to one location to obtain necessary health care information about that patient. Particularly important data are the medical fluid prescriptions ordered for a patient and the status of the infusion of those prescribed medical fluids into the patient. The ability to determine which fluids have been infused, which are being infused, and which are scheduled to be infused in the future is very useful to the nurse. The ability to examine all of this information on one monitor next to the patient has been found to provide a large increase in efficiency of nurses and other care giving professionals. Patient data management systems strive to continually provide such information and allow for different, selectable, formats of presentation of that data. Automation in gathering this data and updating such data is desired. Nurses have extremely busy schedules and automating as much data gathering and presentation as possible is highly desirable.

One area of desired data presentation mentioned above is the ability to display at the bedside PDMS monitor the status of all infusion pumps engaged with the patient. Presently, many infusion pumps have the ability to communicate with other data systems. For example, the Medley® Point-of-Care system distributed by ALARIS Medical Systems, San Diego, Calif., U.S.A., is able to communicate wirelessly through RF. Other pumps are able to communicate in hard-wired modes and through other wireless means, such as IR. Communicated data differs among pumps and not all pumps are able to communicate all of the data desired to be displayed on PDMS bedside monitors at present. Health care facilities using patient data management systems in some cases desire that a precise identification of each ongoing infusion be displayed at the bedside PDMS monitor, as well as the status of the infusion pump (for example "alarming" or "standby"), the progress of infusions (for example, the volume infused), the pumping parameters of the infusion (for example, the rate of infusion, volume to be infused), and possibly other information. In the identification of the infusion, PDMS users often desire that the name of the medical fluid and the dose be made available to the bedside PDMS system directly from the programmed pump 58. Such a feature results in further automation thereby reducing the workload on nurses.

It is this identification and communication of the infusion medical fluid and its dose by the pump that some pumps are unable to satisfy. Many pumps today, such as the Asena® infusion pump distributed by ALARIS Medical UK, Basingstoke, United Kingdom, contain a library of drug names (medical fluids) and are able to present a list of drug names on the front display of the infusion pump from which the pump operator may select the fluid being infused. However, as discussed above in the Background section, the list of drug names used by physicians and health care facilities is extremely large and some physicians assign their own names to specialized drug combinations so that no standard list is likely to contain the name. Nevertheless, health care facilities desire that the drug name being infused by each pump connected to a patient is displayed on the bedside PDMS monitor so that a nurse need only view that one monitor and need not resort to some other data source to determine which drug and what dose is being infused into the patient. The ability to transfer information about the activities of an infusion pump is generally referred to as "connectivity" of the infusion pump. There are various degrees of connectivity and infusion pumps that transfer data concerning desired infusion data have more "connectivity" than infusion pumps that do not transfer such data.

Figure 5:
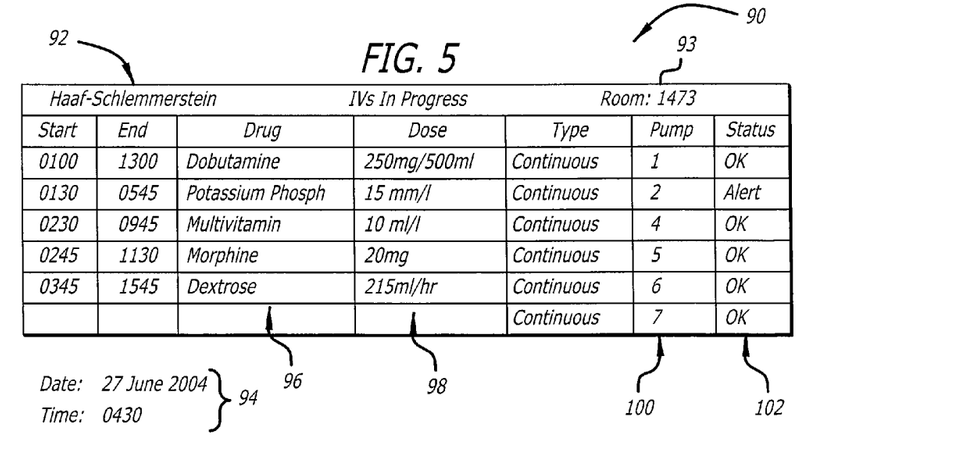
FIG. 5 shows a patient data management system monitor display of the medical fluids being infused into a particular patient and providing the identification of the pump used to infuse the particular drug into the patient.

An example of the type of data to be presented on the bedside PDMS monitor 52 relating to an association of a pump with the name of the drug it is infusing is shown in FIG. 5. A screen 90 of patient-related infusion data is presented. In particular, the patient's name 92 is prominently shown along with his or her location 93 and the date and time 94. The names of drugs 96 and their doses 98 being infused into the patient are also shown. The association of each drug with a particular pump 100 is also shown along with the pump status. In this case, the status shown is "OK" or "Alert"; however, other status may be shown. The screen display 90 thus shows an association of the patient with a drug 96 being infused into the patient with the pump 100 used to infuse the drug into the patient. Other patient infusion data may be included in such a screen display, such as a patient identification number.

Figure 6:
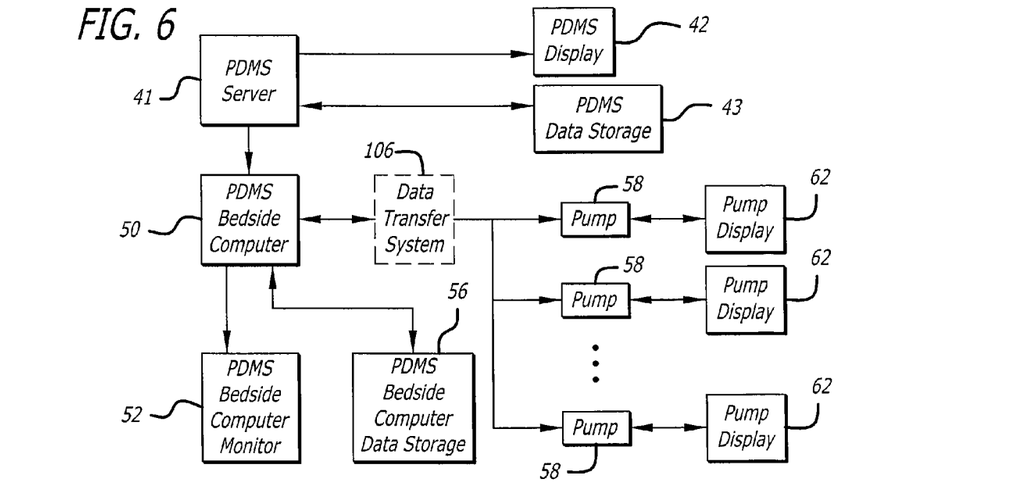
FIG. 6 shows a data transfer system in accordance with aspects of the invention situated to provide associations of pump, patient, and medical fluid to the patient data management system to which it is connected.

In many pumps today, the pump programmer selects the name of the fluid to be infused into the patient from a library of names stored in the pump. The programmer selects the correct drug name from that library and that name is displayed by the pump on its front panel. While it is most desirable that the infusion pump then directly transfer the name of the drug and dose that it is infusing to the PDMS 44, it is acceptable if the name arrive at the monitor 52 of the bedside PDMS system through other means, as long as accuracy exists. Referring now to FIG. 6, a data transfer system 106 has been positioned between the infusion pumps 58 and the PDMS bedside computer 50. The purpose of the data transfer system is to provide a system and a method to associate the drug name with a patient and with a pump used to infuse the drug into the patient. The resulting association is made available to the bedside PDMS monitor 52 for display to care givers.

Figure 7:
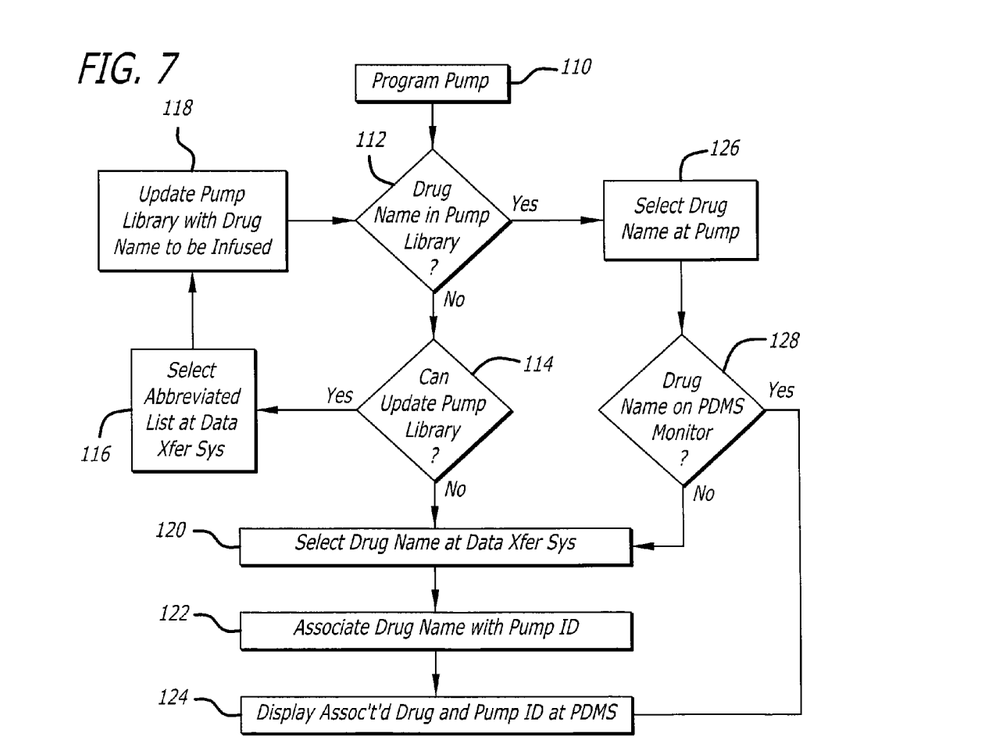
FIG. 7 shows a method and the operation of the data transfer system in accordance with the invention providing detail on associating patient with medical fluid and with pump.

Referring to the block diagram and flow chart of FIG. 7, a system and method in accordance with aspects of the invention are shown. In the course of providing medical care to a patient, an infusion pump is programmed 110 to infuse a drug under certain pumping parameters, such as a programmed flow rate. A determination is made as to whether the name of the drug to be infused resides in the drug library of the pump 112. If not, a determination is made as to whether the pump can be updated by uploading the drug name 114. If the pump can receive updates to its drug library, the data transfer system 106 may be used to provide such updates. To avoid the problem discussed above regarding overload of processor capabilities to process large amounts of drug library names, the data transfer system in accordance with one aspect of the system 106 will only upload a single drug name or an abbreviated list of drug names to the pump 116. The reduced-size health care facility standard drug name list may be uploaded in one embodiment. In many cases, this list comprises one-hundred names or fewer and is the list of drugs most often used in the facility. However, the data transfer system 106 in accordance with another aspect of the invention determines if the present drug to be infused is included on the standard list. If so, the data transfer system uploads the standard list to the pump library 118.

In the case where the name of the drug to be infused is not included on the standard drug list of the health care facility, the data transfer system 106 in accordance with another aspect of the invention, will query the PDMS at the bedside PDMS computer 50 or through that computer to the PDMS server 41 to obtain a list of the prescriptions for the patient. That list of prescribed drugs is then displayed on the PDMS bedside monitor 52 for selection by the pump operator. The operator may then select the drug name from the list and then instruct the data transfer system 106 to upload 118 the drug name to the pump for display by the pump on its integral display 62 and for use by the pump in relaying the name of the drug to be infused along with the pump identification to the PDMS computer 50. The PDMS then associates the drug name with the pump and the patient for display on the bedside PDMS monitor, as shown in FIG. 5.

On the other hand where the pump cannot accept an upload of a drug list under normal use conditions, the data transfer system 106 in accordance with aspects of the invention provides the PDMS 40 with the necessary association of patient, drug name, and pump. Moving to block 120 on FIG. 7, the data transfer system queries the PDMS for a list of all prescribed drugs for the patient. The abbreviation "xfer" is used to indicate the word "transfer." Similarly, the abbreviation "ID" is used to indicate the word "identification." This list is presented on the bedside PDMS monitor 52. The pump operator may there select the correct name of the drug to be infused from the displayed list through use of a keyboard, mouse, touch screen, or other means. Once selected, the data transfer system 106 associates 122 the selected drug with the patient and the pump. The pump identification is standard data that is communicated by most infusion pumps. The patient will, in many cases, have already been identified to the PDMS, but patient identification could be confirmed. The data transfer system in accordance with the invention then communicates 124 to the PDMS the preceding data. That is, the data transfer system informs the PDMS that the pump having the particular identification is infusing the drug name to the particular patient name and thereby associates all of this data for use and display by the PDMS. The dose of the drug may also be communicated depending on the configuration of the PDMS.

The data transfer system 106 continually monitors the pump performance and continually passes the appropriate data to the PDMS. For example, the data transfer system is in communication with the pump and senses when the pump has been started for conducting the infusion. For example, the system may monitor the pump for activation of a "pump start" switch used to commence infusion of medical fluid into the patient. The data transfer system then communicates the pump START configuration to the PDMS for display to the nursing staff, in accordance with standard PDMS protocol and as requested by the nurse. The data transfer system may also communicate other information to the PDMS such as an ALERT status of the pump, or a RESTART status, and other information. The data transfer system thus provides the PDMS with all the information it needs to present the necessary infusion data to the nursing staff. The data transfer system provides an interface between the pump and the PDMS that remedies a situation where a pump is unable to provide all the necessary data required by the PDMS to keep the nursing staff informed of infusions.

In the event that the drug to be infused is already in the drug library of the pump 112, either because the library contained it initially or it has been added, the pump operator may select it 126 in accordance with normal operating procedure. This typically has the effect of displaying that drug name on the display screen 62 of the pump. However, in the event that the pump does not have the capability to communicate the selected drug name to the PDMS 128 so that it may be displayed on the PDMS bedside monitor 52 and elsewhere in the PDMS 40, the data transfer system 80 performs the method described above to associate the patient with the medical fluid name and with the pump 120, 122, and 124 so that the PDMS will be enabled to display this information to the nursing staff.

In the event that the pump 58 has complete connectivity and once the drug name is selected at the display screen 62 of the pump, it is communicated to the PDMS 40 by the pump and displayed there 124, no further action is necessary.

In a further embodiment, the data transfer system 106 maintains or cancels the association between the infusion pump and the medical fluid name depending on the logged changes in the operating status of the pump. In most, if not all, pumps, a log exists in which all events of the pump are stored. Typically the log resides in an internal memory of the pump that can be accessed to determine the status of the pump over many days, weeks, and sometimes months, depending on the level of usage of the pump. Each "event" of the pump is logged. An event includes switch presses, sensor readings, programming, and other events. Such events can be found in the log files contained inside the pump and those log files are automatically updated by the pump with every change in operating status of the pump. In accordance with one embodiment, the data transfer system 106 monitors the infusion pump log to obtain status of the infusion into the patient and if the infusion pump is disconnected from communication with the PDMS before the infusion is complete and is then reconnected with the PDMS, the data transfer system will maintain the association between the infusion pump and the medical fluid name if the status of the pump shows that neither a pumping parameter nor the patient nor the medical fluid name were changed during the time of communication disconnection, and will cancel the association between the infusion pump and the medical fluid name if the status of the pump shows that a pumping parameter or the patient or the medical fluid name was changed during the time of communication disconnection. When the association of the pump with the medical fluid name is broken, the PDMS will indicate that the pump is operating but the PDMS does not have a medical fluid name. The PDMS may indicate such a status by circling a pump icon, blinking the pump icon, using a different color for the pump icon or otherwise communicating that the pump status need to be updated on the PDMS.

In a further feature, the data transfer system 106 provides a means for the case where the length of the character sequence identifying a single medical fluid name of the list of medical fluid names to be stored in the pump exceeds the character sequence length limit defined by the pump. In this case the transfer data system will automatically abbreviate the drug name to a human readable drug name with a length capable of being stored inside the pump, including a unique identifier or code. In one embodiment, both the abbreviated medical fluid name and the unique identifier are human and machine readable. Also in an embodiment, the unique identifier comprises a unique checksum of the non-abbreviated drug name. The checksum will be different for all non-abbreviated drug names and therefore the abbreviation of two or more drug names that may have the same abbreviated character sequence can be distinguished. By this checksum, two or more abbreviated drug names with the same character sequences will be distinguishable by their checksum, which will be different when the non-abbreviated drug names are different.

Yet further, the data transfer system 106 will maintain a table containing pairs of non-abbreviated drug names and abbreviated drug names with the correct checksum identifier. The table will be used to convert a pump reading of an abbreviated drug name with the checksum into the non-abbreviated drug name.

In yet a further embodiment, the data transfer system 106 uploads pumping parameters to the pump for programming the pump. Pumping parameters are meant to include those parameters that concern delivery of the medical fluid to the patient by operation of the pump. For example, flow rate and volume to be infused are pumping parameters. Depending on the pump capabilities, the pump may be programmed by the uploaded pumping parameters and will begin operation as soon as the start switch is pressed by an operator. Entire pumping protocols may be uploaded by the data transfer system. In another embodiment, the pump may include an integral drug library that includes limits on pumping parameters. Such limits may be organized by drug name or by other criteria. Uploaded pumping parameters or other data of a protocol are compared against the drug library and if a parameter exceeds the limits permitted by the library, an alarm is given. The drug library and the comparisons may all take place internally to the pump. However, other approaches may be used where the drug library and comparisons of pumping parameters to it are located outside the pump. Such a library and comparison system is available from ALARIS Medical System, Inc., San Diego, Calif., U.S.A., and ALARIS Medical, UK, Basingstoke, UK In a further embodiment, the transmission of data between the data transfer system 106 and the pump 58 may be secure. Encryption may be used to secure the transmissions or other approaches may be used to result in secure data transmission.

The data transfer system 106 in accordance with the invention may take different forms. In one preferred embodiment, it may take the form of software that executes on the bedside PDMS computer. This is preferred since the computer already exists and no additional hardware would be required. In another case, a PDMS need not be used. The system and method in accordance with other aspects of the invention may be employed on systems other than a PDMS. Other forms are possible.

Although the term "medical fluid" and the term "drug" are used in this patent application, no distinction is meant to be drawn between the two. The term "drug" is not meant to be limited to a fluid containing a medicine and may apply to other treatment or diagnosis fluids that are infused into a patient. For example, the inventor intends that the term "drug" apply to a life sustaining fluid such as dextrose as well as to a treatment fluid such as Adrenaline.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While variations have been described and shown, it is to be understood that these variations are merely exemplary of the present invention and are by no means meant to be limiting.

What is claimed is:

1. A method of associating a name of a medical fluid with an identification of an infusion pump used to infuse the medical fluid into a patient, comprising:
    identifying an infusion pump as being connected to the patient;
    monitoring the infusion pump for an indication by the infusion pump of the name of the medical fluid for infusion into the patient;
    determining if the infusion pump can be updated by uploading the name of the medical fluid;
    uploading, via a computer network, if the infusion pump can be updated, the name of the medical fluid to the infusion pump;
    displaying, if the infusion pump cannot be updated, a plurality of selectable medical fluid names comprising the name of the medical fluid on a monitor that is separately located from the infusion pump;
    selecting, if the infusion pump cannot be updated, the name of the medical fluid from the separate monitor;
    associating, if the infusion pump cannot be updated, after said selecting, the name of the medical fluid with the identification of the infusion pump; and
    providing, if the infusion pump cannot be updated, after said associating, the name of the medical fluid and the identification of the infusion pump to a patient data management system ("PDMS") for display of the name of the medical fluid and the associated identification of the infusion pump on a monitor that is separately located from the infusion pump.

2. The method of claim 1 wherein:
    the step of monitoring the infusion pump also comprises monitoring the infusion pump with a computer external from the infusion pump for an indication of a start of an infusion into the patient; and
    upon detecting the indication of start of infusion, then performing the step of associating the selected medical fluid name with the identification of the infusion pump.

3. The method of, claim 2 wherein the indication of the start of an infusion is detected when a start infusion switch is pressed on the infusion pump.

4. The method of claim 1 wherein the step of displaying at least one selectable medical fluid name on a separate monitor comprises displaying a list of medical fluid names that have been prescribed for the patient.

5. The method of claim 1 wherein the step of displaying at least one selectable medical fluid name on a separate monitor comprises displaying a list of names of standard medical fluids.

6. The method of claim 5 wherein the step of displaying a list of standard medical fluid names comprises displaying an abbreviated list of medical fluid names selected by a health care facility in which the infusion pump is located.

7. The method of claim 1 wherein the step of uploading the selected medical fluid name to the pump comprises abbreviating the selected medical fluid name to a smaller number of characters when the number of characters in the non-abbreviated medical fluid name exceeds a predetermined limit number, and adding an identifier to the abbreviated name that is unique to the non-abbreviated medical fluid name before uploading the medical fluid name to the pump.

8. The method of claim 7 further comprising the step of comparing at the pump the abbreviated name and identifier uploaded to the pump to a table stored in the pump that contains such abbreviated names and identifiers corresponding to the non-abbreviated medical fluid names, in which table different medical fluid names may have identical abbreviated names but the identifiers are always different to thereby distinguish between different medical fluid names having the same abbreviated names.

9. The method of claim 1 further comprising:
    uploading at least one pumping parameter to the pump; programming the pump with the uploaded pumping parameter for infusing the medical fluid to the patient;
    communicating the uploaded pumping parameter to the PDMS; and associating the selected pumping parameter with the identification of the infusion pump and the selected medical fluid name at the PDMS for display of the uploaded medical fluid name, the pumping parameter, and associated identification of the infusion pump on the separately-located monitor.

10. The method of claim 9 further comprising: comparing the uploaded pumping parameter to a data base of predetermined pumping parameter limits; and providing an alert if the uploaded pumping parameter is outside the limits.

11. The method of claim 10 further comprising storing the data base of predetermined pumping parameter limits within the pump.

12. The method of claim 1 further comprising:
    monitoring the infusion pump to obtain status of the infusion into the patient and if the infusion pump is disconnected from communication with the PDMS before the infusion is complete and is then reconnected with the PDMS:
    maintaining the association between the infusion pump and the medical fluid name if the status of the pump shows that neither a pumping parameter nor the patient nor the medical fluid name were changed during the time of communication disconnection; and canceling the association between the infusion pump and the medical fluid name if the status of the pump shows that a pumping parameter or the patient or the medical fluid name was changed during the time of communication disconnection.

13. The method of claim 12 wherein the step of monitoring the infusion pump to obtain the status of the infusion pump during a time of disconnection from the PDMS comprises monitoring a log of the infusion pump.

14. A fluid infusion monitoring system in which a name of a medical fluid is associated with an identification of an infusion pump used to infuse the medical fluid into a patient, comprising:

a monitor separately located from the infusion pump; and a computer in communication with the infusion pump and in communication with a patient data management system, wherein the computer is programmed to:

identify an infusion pump as being connected to the patient;

monitor the infusion pump for an indication by the infusion pump of the name of the medical fluid for infusion into the patient;

determine if the infusion pump can be updated by uploading the name of the medical fluid;

display, if the infusion pump cannot be updated, a plurality of selectable medical fluid names comprising the name of the medical fluid on the separately-located monitor;

upload, via a computer network, if the infusion pump can be updated, the name of the medical fluid to the infusion pump;

receive a selection of, if the infusion pump cannot be updated, the name of the medical fluid from the separately-located monitor;

associate, if the infusion pump cannot be updated, the name of the medical fluid with the identification of the infusion pump; and provide, if the infusion pump cannot be updated, after said association, the name of the medical fluid name and the identification of the infusion pump to a patient data management system ("PDMS") for display of the name of the medical fluid and the associated identification of the infusion pump on a monitor that is separately located from the infusion pump.

15. The fluid infusion monitoring system of claim 14 wherein the computer is also programmed to:

monitor the infusion pump for an indication of a start of an infusion into the patient; and upon detecting the indication of start of infusion, then associate the selected medical fluid name with the identification of the infusion pump.

16. The fluid infusion monitoring system of claim 15 wherein: the infusion pump has a start infusion switch; and the computer is programmed to monitor the infusion pump for the press of a start-infusion switch on the infusion pump to indicate the beginning of an infusion.

17. The fluid infusion monitoring system of claim 14 wherein the computer is further programmed to display a list of medical fluid names that have been prescribed for the patient on the separately-located monitor.

18. The fluid infusion monitoring system of claim 14 wherein the computer is further programmed to display a list of names of standard medical fluids on the separately-located monitor.

19. The fluid infusion monitoring system of claim 18 wherein the computer is programmed to display an abbreviated list of medical fluid names selected by a health care facility in which the infusion pump is located on the separately-located monitor.

20. The fluid infusion monitoring system of claim 14 wherein the computer is further programmed to abbreviate the selected medical fluid name to a smaller number of characters when the number of characters in the non-abbreviated medical fluid name exceeds a predetermined limit number, and add a identifier to the abbreviated name that is unique to the non-abbreviated medical fluid name before uploading the medical fluid name to the pump.

21. The fluid infusion monitoring system of claim 20 further comprising a table stored in the pump that contains such abbreviated names and identifiers corresponding to the non-abbreviated medical fluid names, in which table different medical fluid names may have identical abbreviated names but the identifiers are always different to thereby distinguish between different medical fluid names having the same abbreviated names.

22. The fluid infusion monitoring system of claim 14 wherein the computer is further programmed to:

upload at least one pumping parameter to the pump relevant to the selected medical fluid for infusion into the patient by the pump; and associate the uploaded pumping parameter with the identification of the infusion pump and the selected medical fluid name at the PDMS for display of the uploaded medical fluid name, the pumping parameter, and associated identification of the infusion pump on the separately-located monitor.

23. The fluid infusion monitoring system of claim 22 further comprising: a data base of predetermined pumping parameter limits; a processor programmed to compare the uploaded pumping parameter to the data base and provide an alert if the uploaded pumping parameter is outside the limits.

24. The fluid infusion monitoring system of claim 22 wherein the data base of predetermined pumping parameter limits is stored within the pump.

25. The fluid infusion monitoring system of claim 14 wherein the computer is further programmed to:

monitor the infusion pump to obtain status of the infusion into the patient and if the infusion pump is disconnected from communication with the PDMS before the infusion is complete and is then reconnected with the PDMS:

maintain the association between the infusion pump and the medical fluid name if the status of the pump shows that neither a pumping parameter nor the patient nor the medical fluid name were changed during the time of communication disconnection; and cancel the association between the infusion pump and the medical fluid name if the status of the pump shows that a pumping parameter or the patient or the medical fluid name was changed during the time of communication disconnection.

26. The fluid infusion monitoring system of claim 25 wherein the computer is programmed to monitor a log of the infusion pump to determine the status of the infusion pump during the time that it was disconnected from the PDMS.

* * * * *